United States Patent [19]

Garza, Jr. et al.

[11] Patent Number: 6,084,122
[45] Date of Patent: Jul. 4, 2000

[54] SULFUR REMOVAL PROCESS FROM AN ACRYLATE WASTE STREAM

[75] Inventors: Martiniano Garza, Jr., Houston; Michael Joseph Barber, Friendswood; Stephen Joseph Markovich, Houston; Steven E. Parker, Seabrook; Hermelinda Pedraza; Carolyn Supplee, both of Corpus Christi, all of Tex.

[73] Assignee: Celanese International Corporation, Dallas, Tex.

[21] Appl. No.: 08/961,596

[22] Filed: Oct. 31, 1997

[51] Int. Cl.⁷ .................................................. C07C 67/48
[52] U.S. Cl. .............................................................. 560/218
[58] Field of Search ............................................. 560/218

[56] References Cited

U.S. PATENT DOCUMENTS

| | | | |
|---|---|---|---|
| 3,450,749 | 6/1969 | Furrow | 260/513 |
| 3,888,917 | 6/1975 | Fentress et al. | 260/504 |
| 4,212,821 | 7/1980 | Marquis et al. | 260/570 |
| 4,450,047 | 5/1984 | Malzahn | 203/15 |
| 4,885,383 | 12/1989 | Weber et al. | 560/103 |
| 5,075,416 | 12/1991 | Staeglich et al. | 528/179 |
| 5,386,052 | 1/1995 | Sakakura | 560/205 |
| 5,434,279 | 7/1995 | Wimmer | 554/169 |

FOREIGN PATENT DOCUMENTS

| | | |
|---|---|---|
| 0 331 864 A1 | 1/1989 | European Pat. Off. . |
| 0 736 523 A2 | 3/1996 | European Pat. Off. . |
| 50-115689 | 9/1975 | Japan . |
| 54-009219 | 1/1979 | Japan . |
| 6234699 | 2/1993 | Japan . |
| 0 6234700 | 8/1994 | Japan . |

*Primary Examiner*—Paul J. Killos
*Attorney, Agent, or Firm*—M. Susan Spiering

[57] ABSTRACT

Broadly, the present invention is directed to a process for the removal of sulfur from an acrylate waste stream. In particular, disclosed is a process for the recovery and reuse of an acid catalyst employed primarily in the reaction of acrylic esters. During the reaction of acrylic acid and an alcohol in the presence of an acid catalyst, the product acrylate and water are removed from the remaining reaction by-products (heavy ends and oligomers). These by-product heavy end components which include the acid catalyst employed in the reaction process, are directed to an evaporator. The residue stream therefrom is then contacted with water in an extractor. Upon contact with water, a phase separation occurs between the acid catalyst/water mixture and other organic matter. The organic matter is discarded while the acid/water mixture is recycled to the reaction process.

The present invention employs the use of an evaporator and an extractor to aid in the separation of the acid catalyst from the reaction by-products waste stream. This removal of acid results in fewer organic sulfur components to be emitted from the reaction process and hence is a more environmentally friendly process.

7 Claims, No Drawings

SULFUR REMOVAL PROCESS FROM AN ACRYLATE WASTE STREAM

FIELD OF THE INVENTION

This invention relates to an improved process for producing acrylic esters. More particularly, this invention provides a method for removal of sulfur from an acrylate waste stream. The sulfur is typically in the form of an alkanesulfonic acid compound, and is generally used as an acid catalyst for the esterification reaction. This acid catalyst may be efficiently recovered and reused via the disclosed process.

BACKGROUND OF INVENTION

Esterification reactions for the production of acrylic esters are well known in the art. The esterification generally involves the reaction of an (meth)acrylic acid and alcohol having 4 or more carbon atoms, in the presence of a strong acid as a catalyst to produce the corresponding ester desired. U.S. Pat. No. 5,386,052, herein incorporated by reference in its entirety, describes the reaction generally, and claims a process for producing acrylic or methacrylic esters. Examples of acids employed in the reaction process include, but are not limited to sulfuric acid, p-toluenesulfonic acid, benzenesulfonic acid, xylenesulfonic acid, naphthenesulfonic acid, methanesulfonic acid, and the like. In a continuous process, these strong acids are removed from the reaction liquid by way of an organic purge taken to maintain oligomer and polymer concentrations in the reaction liquid. This organic purge is then disposed of by some appropriate method. Currently, most methods of disposal have an environmental impact.

U.S. Pat. No. '052 also describes a method for the removal of the acid whereby the reaction liquid (containing a predominantly desired ester product) is washed with water, separated from the aqueous solution containing the acid catalyst, and recycling the aqueous solution.

Also described in U.S. Pat. No. '052 is a method for removing the strong acid in which the reaction liquid is treated with an aqueous alkaline solution for neutralization (Japanese Laid-Open Patent Publications Nos. 243046/1986, 34965/1991 and 230240/1992). According to this method, a large amount of alkali is needed for effecting a sufficient neutralization. Moreover, it is very difficult to separate and recover the acid catalyst and unreacted acrylic or methacrylic acid from the aqueous alkaline solution after the treatment and, therefore, the aqueous alkaline solution must be disposed as a waste after the treatment. A drawback of this method is the production of a large amount of waste water which contains a high concentration of potentially harmful organic acid salts.

Due to the above drawbacks, it is desirable to remove as much sulfur containing compounds from process steams as possible, so as to minimize environmental impact(s). It is also desirable to recover and reuse the acid catalyst so as to reduce the overall costs involved in the esterification reaction, as well as reduce the labor and expense involved in any acid disposal.

SUMMARY OF THE INVENTION

In the esterification reaction to produce butyl acrylate (BA), acrylic acid and butanol (BuOH) are reacted in the presence of a catalyst; generally methanesulfonic acid (MSA). A heavy ends purge stream (traditionally considered, and also referred to as a waste stream since it contains oligomers and polymers of BA, plus minor amounts of desired ester product) is taken from the reaction to remove any oligomer and polymeric buildup in the reactor. MSA catalyst is present in this organic purge stream at a given concentration. Traditionally, this purge stream has been incinerated for disposal. We have now discovered a process to recover the MSA in an environmentally friendly, cost efficient, and commercially viable manner. MSA is recovered by a water extraction process employing a liquid—liquid extractor and a recycled internal water stream.

The organic/MSA purge stream is allowed to contact and mix with the recycled process water stream. The mixture is then directed into a decanter for phase separation. A separable phase is formed between the water/MSA phase and the organic purge waste stream from the butyl acrylate reaction process. The MSA/water phase is then recycled to the esterification reaction process. Extracted MSA/water samples have shown high recoveries of MSA (up to 90%). Other components recovered include butanol, butyl acrylate, and acrylic acid. The recovery process may employ mechanical equipment such as a continuous stirred tank reactor (CSTR), static in-line mixer (SILM), or an agitated liquid—liquid counter current extractor to achieve the organic/water mixture. Although this process is discussed in terms of recovery of MSA and the reaction to form butyl acrylate, it can also be employed for the recovery of other acids, particularly other alkanesulfonic acids and in the reaction to form other (homolog) esters.

The present invention is directed to a process for the removal of sulfur from an acrylate waste stream comprising:
(a) contacting in a reactor (meth)acrylic acid with an alcohol having four or more carbon atoms in the presence of an acid catalyst to form a reaction mixture containing the corresponding ester reaction product and residue byproducts;
(b) removing the reaction product from the reaction mixture by distillation;
(c) directing the residue of the reaction mixture to an evaporator;
(d) directing the residue of (c) to an extractor and contacting with water to form a two phase system comprising as phase (1) acid catalyst/water, and as phase (2) heavy ends and oligomers; and,
(e) recycling phase (1) of (d) containing acid catalyst to the reactor of (a).

More particularly, the invention is directed to removal and optionally recycle of methane sulfonic acid from a butyl acrylate waste stream.

The present invention employs the use of an liquid—liquid extractor to aid in the separation of the acid catalyst from the reaction by-products. The removal of acid (which contains sulfur) results in fewer organic sulfur components to be emitted from the reaction process and hence is a more environmentally friendly process. Accordingly, the acid catalyst used for the esterification reaction and unreacted (meth)acrylic acid can be effectively recovered and reused for the reaction. The amount of catalyst to be used in the reaction process can be considerably reduced. More importantly, this process eliminates the amount of sulfur species present in the treated evaporator waste stream.

DETAILED DESCRIPTION OF THE INVENTION

The present process involves separation and recovery of mixtures of MSA, butanol (BuOH), butyl acrylate (BA), and acrylic acid by liquid—liquid extraction using a process water stream. The residue or waste stream, is obtained from a BA manufacturing processing involving the use of an acid catalyst (e.g., MSA) for the reaction of BuOH and acrylic acid.

The present invention is directed to a process for the removal of sulfur from an acrylate waste stream.

In an aspect of the inventive reaction process, an alcohol having 4 or more carbon atoms is reacted with an (meth) acrylic acid in the presence of an acid catalyst to form an acrylate ester; said acid catalyst containing at least one sulfur moiety. In the present invention, any alcohol selected from aliphatic, alicyclic and aromatic alcohols can be used as the alcohol having 4 or more carbon atoms. Examples of the aliphatic alcohols include but are not limited to butyl alcohol, pentyl alcohol, hexyl alcohol, heptyl alcohol, octyl alcohol, 2-ethylhexyl alcohol, nonyl alcohol, decyl alcohol, dodecyl alcohol, hexadecyl alcohol and stearlyl alcohol. Examples of the alicyclic alcohols include cyclopentyl alcohol, cyclohexyl alcohol, ethylcyclohexyl alcohol, ethylcyclohexyl alcohol and butylcyclohexyl alcohol. Examples of the aromatic alcohols include benzyl alcohol, methylbenzyl alcohol, dimethylbenzyl alcohol and butylbenzyl alcohol.

As the acid catalyst for esterification, toluenesulfonic acid, benzenesulfonic acid, xylenesulfonic acid and methanesulfonic acid are preferably used. Sulfuric acid has frequently been used as a catalyst for esterification. Sulfuric acid is not recommended since it is difficult to efficiently remove from the esterification reaction.

In the esterification reaction between acrylic or methacrylic acid (herein referred to as (meth)acrylic acid) and an alcohol, the starting (meth)acrylic acid and the alcohol are usually supplied to the reaction in the general molar ratio range of about 0.8:1.2. The amount of the acid catalyst used is generally from about 0.1 to 5.0% by weight. The reaction is carried out generally at a temperature of about 120° C. while reaction water produced in the course of esterification is preferably removed by distillation or azeotropic distillation. In order to facilitate the removal of reaction water, an inert azeotropic agent may be used. Hydrocarbons such as benzene, toluene and cyclohexane are commonly used as the azeotropic agent. The removal of reaction water may also be conducted by conventional means such as membrane separation using a vapor separation membrane, or by a method other than distillation. In order to prevent the loss of (meth)acrylic acid or the ester due to the occurrence of unfavorable polymerization thereof, a polymerization inhibitor or an oxygen-containing gas may be added to the reactor.

In the present process, reaction product containing ester (e.g., butyl acrylate if butanol is employed) and water are removed from the top of the reactor. A residue stream containing unreacted alcohol and (meth)acrylic acid, the corresponding ester, the acid catalyst, heavy end oligomers, and a trace amount of any polymerization inhibitor employed is then directed to an evaporator for the recovery of any residual ester product and reactants. This purge stream from the reactor is needed for the removal of polymers that build up during the esterification reaction. The evaporator is operated under vacuum and with elevated temperature to facilitate the recovery of any residual ester product, (meth)acrylic acid and butanol. The residue of the evaporator containing primarily heavy end oligomers is directed to an extractor.

U.S. Pat. No. '052 describes an aqueous stream directed from a reactor to an evaporator. However, the aqueous stream of U.S. Pat. No. '052 is composed primarily of ester product and acid catalyst, with the disclosure being directed to purifying the ester product. No mention is made in U.S. Pat. No. '052 of the purification of the waste stream. U.S. Pat. No. '052 employs a product stream while the present invention employs a waste stream.

According to the present invention, the evaporator residue stream containing the sulfonic acid catalyst is directed to an agitated liquid—liquid extractor wherein water is added to phase separate the sulfonic acid from other components present in the residue. Water is typically added at about a 1:1 ratio of water to organic feed. The organic evaporator residue feed stream temperature is about 140–160° C. The recycled process water added for phase separation is generally at a temperature of about 60–80° C. Mixer rates are variable based on the composition of the mixture to separate, the type of acid employed, the temperatures employed within the extractor, etc. Mixer rates within the extractor should be sufficient to allow mass transfer needed for efficient extractions.

The residue from the evaporator, i.e., the material that is taken out the bottom of the evaporator, is composed of approximately 85% oligomers and the balance BA, MSA and reactants. Acid catalysts is present at about 4–8%.

Because of the MSA content of the evaporator residue, the incinerator emissions can contain a significant amount of sulfur. Removal of the MSA from the evaporator residue will make the BA process more environmentally friendly and save substantial amount of money in disposing of the evaporator waste. The disclosed process removes approximately 80–90% of the MSA from the evaporator residue.

An agitated liquid—liquid counter current extraction column of an ordinary type will suffice for extraction. In a preferred embodiment, the evaporator residue liquid is fed into the extraction column at the upper end thereof, and the water is fed at the lower end of the extraction column. MSA, BA, and BuOH, and acrylic acid are separated from the oligomers and polymers of BA and other organic waste by-products of the BA production process by the water as both phases are mixed. In an embodiment, the mixture is agitated through use of a spinning multipateled shaft or a baffled series of plates. A packed column, a tray tower or the like may be employed as an extraction column; it is preferred to use an apparatus wherein the liquid—liquid contact is effected with high efficiency.

Although fresh water can be used in the extractor, the reaction water (i.e., overhead water from reactor column) produced in the esterification reaction and removed from the reaction system may also be employed in the extractor column for recovery of the sulfonic acid catalyst. The use or recycling of reaction water has the advantage that the amount of waste water in the system can be reduced.

After contact, the water phase containing MSA, BA, BuOH, and acrylic acid is taken from the top of the extractor overhead to a coalescer. The purpose of the coalescer is to allow any organic fines (particulates) present in the water phase to settle out. After settling, the water phase is recycled to the reactor from the overflow of the decanter. The stream taken from the bottom of the decanter is disposed.

The mixture taken as an overhead stream from the decanter is transferred to a phase separator/decanter for separation of the acid/water and the organic waste products. The acid/water is then recycled to the esterification reaction while the organic waste products are transferred for further handling, including disposal thereof. The recovered water/sulfonic acid layer has been found to contain MSA at a concentration range of about 2–10%. The aqueous solution is recycled back to the esterification reaction step, and the catalyst is effectively reused for the reaction. The recovered water contains about 2–6% acrylic acid. Generally, acid catalyst in an amount of about 2 wt % or more is recycled to the reactor based on the initial catalyst fed to the reactor.

We have been able to extract and recover about 80–90% of the MSA initially utilized in the reactor for the esterification reaction process. This covered MSA has been shown to be active and reusable for continued esterification reactions.

What is claimed is:

1. A process for the removal of sulfur from an acrylate waste stream comprising:
   (a) contacting in a reactor (meth)acrylic acid with an alcohol in the presence of an acid catalyst to form a reaction mixture containing the corresponding ester reaction product and residue byproducts;
   (b) removing the reaction product from the reaction mixture;
   (c) directing the residue of the reaction mixture containing the acid catalyst, heavy end oligomers formed during the reaction to an evaporator;
   (d) directing the residue of (c) to an extractor and contacting with water to form a two phase system comprising as phase (1) acid catalyst/water, and as phase (2) heavy end oligomers; and,
   (e) recycling phase (1) of (d) containing acid catalyst to the reactor of (a).

2. A process for e recovery of acid catalyst employed during the production of an acrylic ester comprising:
   (a) contacting in a reactor, (meth)acrylic acid with an alcohol having 4 or more carbon atoms in the presence of an acid catalyst and an aqueous environment to form a reaction mixture containing the corresponding (meth) acrylic ester reaction product and residue byproducts;
   (b) removing the reaction product from the reaction mixture by distillation;
   (c) directing the residue of the reaction mixture containing the acid catalyst, heavy end oligomers formed during the reaction to an evaporator;
   (d) directing the residue of (c) to an extractor and contacting with water to form a two phase system comprising as phase (1) acid catalyst/water, and as phase (2) heavy end oligomers;
   (e) recycling phase (1) of (d) containing acid catalyst to the reactor of (a).

3. The process according to claim 1, wherein the acid catalyst is selected from the group consisting of methanesulfonic acid, benzenesulfonic acid, toluenesulfonic acid and xylenesulfonic acid.

4. The process according to claim 3, wherein the acid is methanesulfonic acid.

5. The process of claim 1 (c) wherein the residue comprises about 85% oligomers and polymers of butyl acrylate, and about 4–8% acid catalyst.

6. The process of claim 1 (d) wherein upon contact of the residue with water to form a mixture, the mixture is agitated by mixing means at a mixing rate sufficient to allow mass transfer needed for extraction of acid catalyst from the residue.

7. The process of claim 1 wherein acid catalyst in an amount of about 2 wt % or more is recycled to the reactor based on initial catalyst fed to the reactor.

* * * * *